United States Patent
Vellaisamy et al.

(10) Patent No.: US 10,557,814 B2
(45) Date of Patent: Feb. 11, 2020

(54) ELECTROCHEMICAL DETECTOR

(71) Applicant: City University of Hong Kong, Kowloon (HK)

(72) Inventors: A. L. Roy Vellaisamy, Kowloon (HK); Shishir Venkatesh, Shatin (HK); Tan Li, New Territories (HK)

(73) Assignee: CITY UNIVERSITY OF HONG KONG, Kowloon (HK)

( * ) Notice: Subject to any disclaimer, the term of this patent is extended or adjusted under 35 U.S.C. 154(b) by 587 days.

(21) Appl. No.: 15/191,935

(22) Filed: Jun. 24, 2016

(65) Prior Publication Data
US 2017/0370872 A1    Dec. 28, 2017

(51) Int. Cl.
*G01N 27/414* (2006.01)
*G01N 27/333* (2006.01)
*G01N 27/30* (2006.01)

(52) U.S. Cl.
CPC ....... *G01N 27/3335* (2013.01); *G01N 27/301* (2013.01); *G01N 27/414* (2013.01)

(58) Field of Classification Search
CPC ............ G01N 27/3335; G01N 27/404; G01N 27/301; G01N 27/414
See application file for complete search history.

(56) References Cited

U.S. PATENT DOCUMENTS

| | | |
|---|---|---|
| 4,214,968 A | 7/1980 | Battaglia et al. |
| 4,921,591 A | 5/1990 | Mochizuki et al. |
| 5,286,365 A | 2/1994 | Shu |
| 5,674,752 A | 10/1997 | Buckley et al. |
| 6,974,716 B2 | 12/2005 | Hsiung et al. |
| 7,598,546 B1 | 10/2009 | Chou et al. |
| 8,154,093 B2 | 4/2012 | Bradley et al. |
| 8,384,409 B2 | 2/2013 | Kummel et al. |
| 2003/0213691 A1* | 11/2003 | Peper ................. G01N 27/3335 204/416 |
| 2005/0263410 A1* | 12/2005 | Hsiung ................ G01N 27/414 205/789 |
| 2006/0011951 A1 | 1/2006 | Hsiung et al. |
| 2006/0046375 A1 | 3/2006 | Chou et al. |
| 2006/0148118 A1 | 7/2006 | Hsiung et al. |
| 2009/0278175 A1* | 11/2009 | Chou ................... G01N 27/414 257/253 |
| 2012/0048733 A1 | 3/2012 | Yu et al. |
| 2013/0164859 A1 | 6/2013 | Johnson et al. |

(Continued)

FOREIGN PATENT DOCUMENTS

WO    2013/081684 A3    6/2013

OTHER PUBLICATIONS

S. Ritjareonwattu, et al. "An Ion Sensitive Organic Field-Effect Transistor Incorporating the Ionophore Valinomycin", IEEE Sensors Journal, 12(5), p. 1181-1186, May (Year: 2012).*

(Continued)

*Primary Examiner* — J. Christopher Ball
(74) *Attorney, Agent, or Firm* — Renner Kenner Greive Bobak Taylor & Weber

(57) ABSTRACT

An electrochemical detector including at least one substance selection structure disposed adjacent or proximate to an electronic device structure, wherein the substance selection structure is arranged to interact with a target substance so as to alter an electrical characteristic of the electronic device structure.

22 Claims, 8 Drawing Sheets

(56) References Cited

U.S. PATENT DOCUMENTS

2013/0210641 A1 8/2013 Rothberg et al.
2014/0370636 A1 12/2014 Dalton et al.

OTHER PUBLICATIONS

P. Lin and F. Yan, "Organic Thin-Film Transistors for Chemical and Biological Sensing", Advanced Materials, 24(1): p. 34-51, January (Year: 2012).*

M. Guzinski, G. Lisak, J. Kupis, A. Jasinski, M. Bochenska, "Lead(II)-Selective Ionosphores for Ion-Selective Electrodes: A Review", Analytica Chimica Acta, vol. 791, 2013, pp. 1-12; DOI: 10.1016/j.aca.2013.04.044.

J. Bobacka, "Conducting Polymer-Based Solid-State Ion-Selective Electrodes", Electroanalysis, vol. 18, 2006, No. 1, pp. 7-18; DOI: 10.1002/elan.200503384.

* cited by examiner

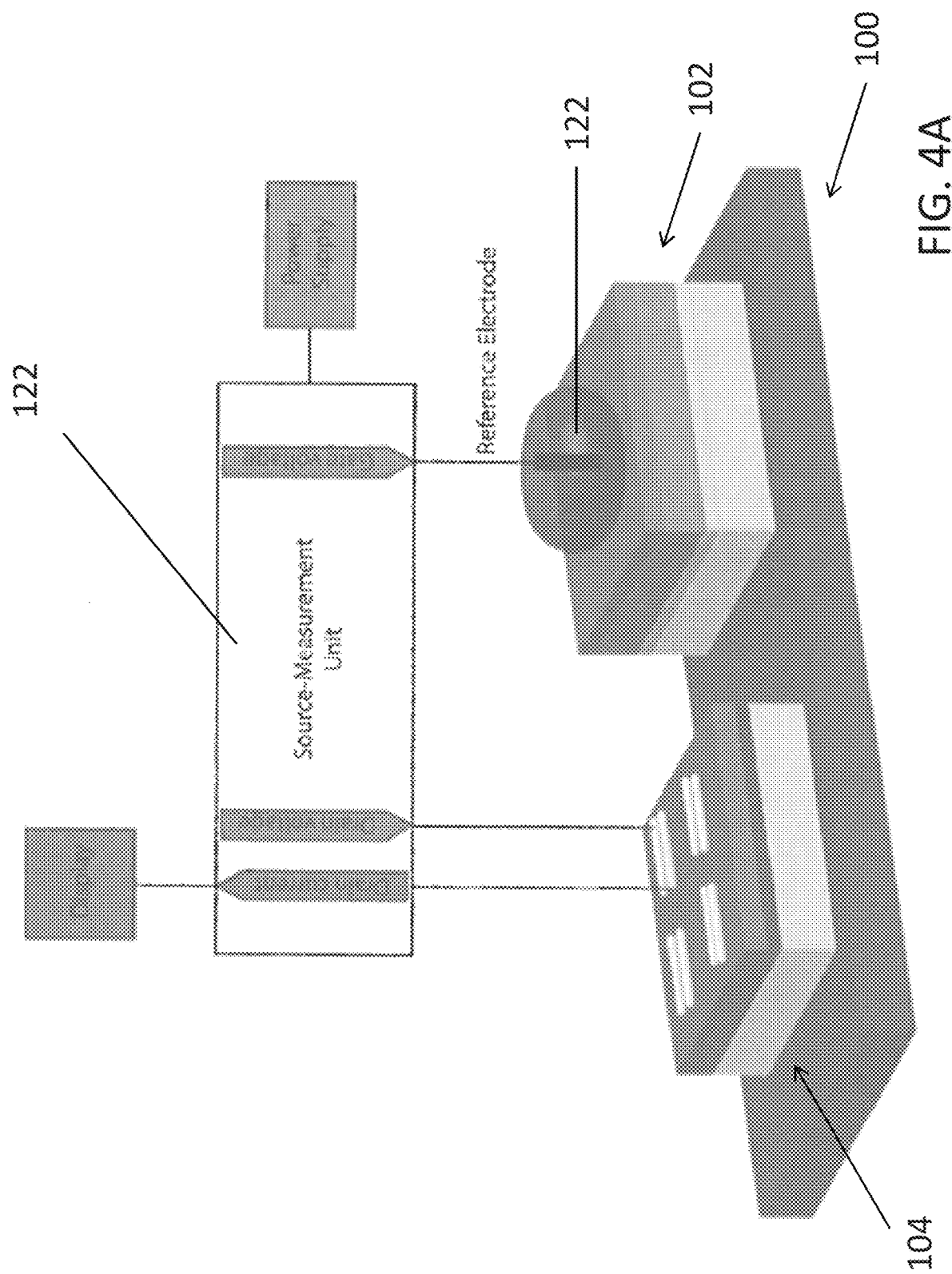

ELECTROCHEMICAL DETECTOR

TECHNICAL FIELD

The present invention relates to an electrochemical detector, although not exclusively, to an electrochemical detector for detecting metal ions in a liquid.

BACKGROUND

Pollution is one of the most serious public health problems in cities around the world. Various pollutants or containments in water may affect the health of the general public. Therefore, the quality of water must be regularly examined to ensure that some poisonous or hazardous pollutants do not exceed safety levels.

The concentration of these pollutants may be determined by using testing agents. The traditional chemical testing approaches are time consuming and may not respond promptly. Alternatively, material characterization techniques in laboratories may be used to analyse the concentration of a target substance and even the composition of a testing sample. Although the results may be very accurate and sensitive, these techniques used in laboratories may not be suitable for daily applications which require prompt and low-cost testing results.

SUMMARY OF THE INVENTION

In one example embodiment, the present invention is advantageous in that it provides for improvement over conventional devices by providing improved detection limit in the neighbourhood of ppb level, without increase in production complexity.

In accordance with a first aspect of the present invention, there is provided an electrochemical detector comprising at least one substance selection structure disposed adjacent or proximate to an electronic device structure, wherein the substance selection structure is arranged to interact with a target substance so as to alter an electrical characteristic of the electronic device structure.

In an embodiment of the first aspect, the at least one substance selection structure arranged to interact with at least one electrically charged chemical ion of the target substance.

In an embodiment of the first aspect, each of the at least one substance selection structure includes an ion-selective electrode.

In an embodiment of the first aspect, the ion-selective electrode comprises an ion-selective membrane arranged to selectively chelate with the at least one electrically charged chemical ion, and wherein the target substance is in contact with the ion-selective membrane.

In an embodiment of the first aspect, the ion-selective membrane includes an ionophore.

In an embodiment of the first aspect, the ionophore is arranged to selectively chelate with the at least one electrically charged chemical ion so as to transport the at least one electrically charged ion across the ion-selective membrane according to an effect of diffusion.

In an embodiment of the first aspect, the ion-selective electrode further comprises an ion-electron transducer arranged to generate a potentiometric signal in response to the interaction between the target substance and the substance selection structure.

In an embodiment of the first aspect, the ion-electron transducer is adjacent to the ion-selective membrane.

In an embodiment of the first aspect, the ion-electron transducer is arranged to receive the at least one electrically charged ion dissociated from the ionophore at an interface between the ion-electron transducer and the ion-selective membrane.

In an embodiment of the first aspect, the ion-electron transducer is arranged to generate the potentiometric signal by transferring at least one electron in response to the reception of the at least one electrically charged ion.

In an embodiment of the first aspect, the ion-electron transducer includes a conductive polymer.

In an embodiment of the first aspect, the potentiometric signal generated by the ion-electron transducer is further transmitted to the electronic device structure so as to alter the electrical characteristic of the electronic device structure.

In an embodiment of the first aspect, the electrochemical detector further comprises an intermediate substrate arranged to connect the at least one substance selection structure and/or the electronic device structure.

In an embodiment of the first aspect, the intermediate substrate includes a copper substrate.

In an embodiment of the first aspect, the intermediate substrate is further arranged to transmit an electronic signal between the at least one substance selection structure and/or the electronic device structure.

In an embodiment of the first aspect, one or more of the at least one substance selection structure and the electronic device structure are fabricated on a plurality of separate substrates.

In an embodiment of the first aspect, the plurality of separate substrates includes a plurality of doped silicon substrates.

In an embodiment of the first aspect, the electronic device structure is a thin-film transistor.

In an embodiment of the first aspect, the at least one substance selection structure is arrange to operate as a gate electrode of the thin-film transistor.

In an embodiment of the first aspect, the electrical characteristic includes a threshold voltage of the thin-film transistor.

In an embodiment of the first aspect, the electrical characteristic includes a saturation drain current across the thin-film transistor under a predetermined gate bias and a predetermined source-drain bias.

In an embodiment of the first aspect, the target substance includes lead ion.

In accordance with a second aspect of the present invention, there is provided a method of detecting a target substance with the electrochemical detector in accordance with the first aspect, comprising the steps of: applying an analyte solution containing a predetermined amount of the target substance to the at least one substance selection structure; applying a gate voltage to the thin-film transistor via the analyte solution and the at least one substance selection structure; applying a source-drain bias to the thin-film transistor; and determining a concentration of the target substance in the analyte solution based on a characterization of the electrical characteristic of the thin-film transistor.

In an embodiment of the second aspect, the method comprises the step of electrically connecting at least two of the substance selection structures in a serial configuration in a gate electrode of the thin-film transistor.

In an embodiment of the second aspect, the gate voltage is applied to the analyte solution applied on a first substance selection structure and the thin-film transistor is electrically connected to a second substance selection structure via the analyte solution applied on the second substance selection structure.

In an embodiment of the second aspect, an overall capacitance subjected by the thin-film transistor is reduced such that the detection limit of the determination of the concentration of the target substance is decreased.

BRIEF DESCRIPTION OF THE DRAWINGS

Embodiments of the present invention will now be described, by way of example, with reference to the accompanying drawings in which:

FIG. 4A is an illustration showing a first example operation of detecting a target substance with the electrochemical detector of FIG. 1;

DETAILED DESCRIPTION OF THE PREFERRED EMBODIMENT

The inventors have, through their own research, trials and experiments, devised that the amount of lead or the active Pb (II) ions is an important parameter to assess from the perspective of public health safety. Conventional methods of detection include Ion Mobility Spectrometry (IMS) and its variants, Ion Chromatography and its variants, Surface Enhanced Raman Scattering (SERS) technology, Spectrophotometric methods, etc. However, most of the previously mentioned technologies are restrictive in terms of cost, time and end-user training. Therefore, cheap, quick and user friendly technologies for Pb (II) detection in water are in great demand.

Preferably, thin film transistor (TFT) based sensors may be used due to their low cost and simple fabrication process. On the other hand, modular design which may enable the combinations to different types of chemical receptors for different applications. In addition, these modular devices may be fabricated by printing in large and flexible substrates.

In one example embodiment of the present invention, electrochemical sensors based on selective bonding in aqueous phase to detect Pb (II) ions are provided. The sensor may be used to detect extremely low levels (ppb) of Pb (II) with appropriate receptors or sensing electrodes, thus providing a cost-effective, accurate and reliable means for the Pb (II) detection in water or other liquids.

Figure 1:
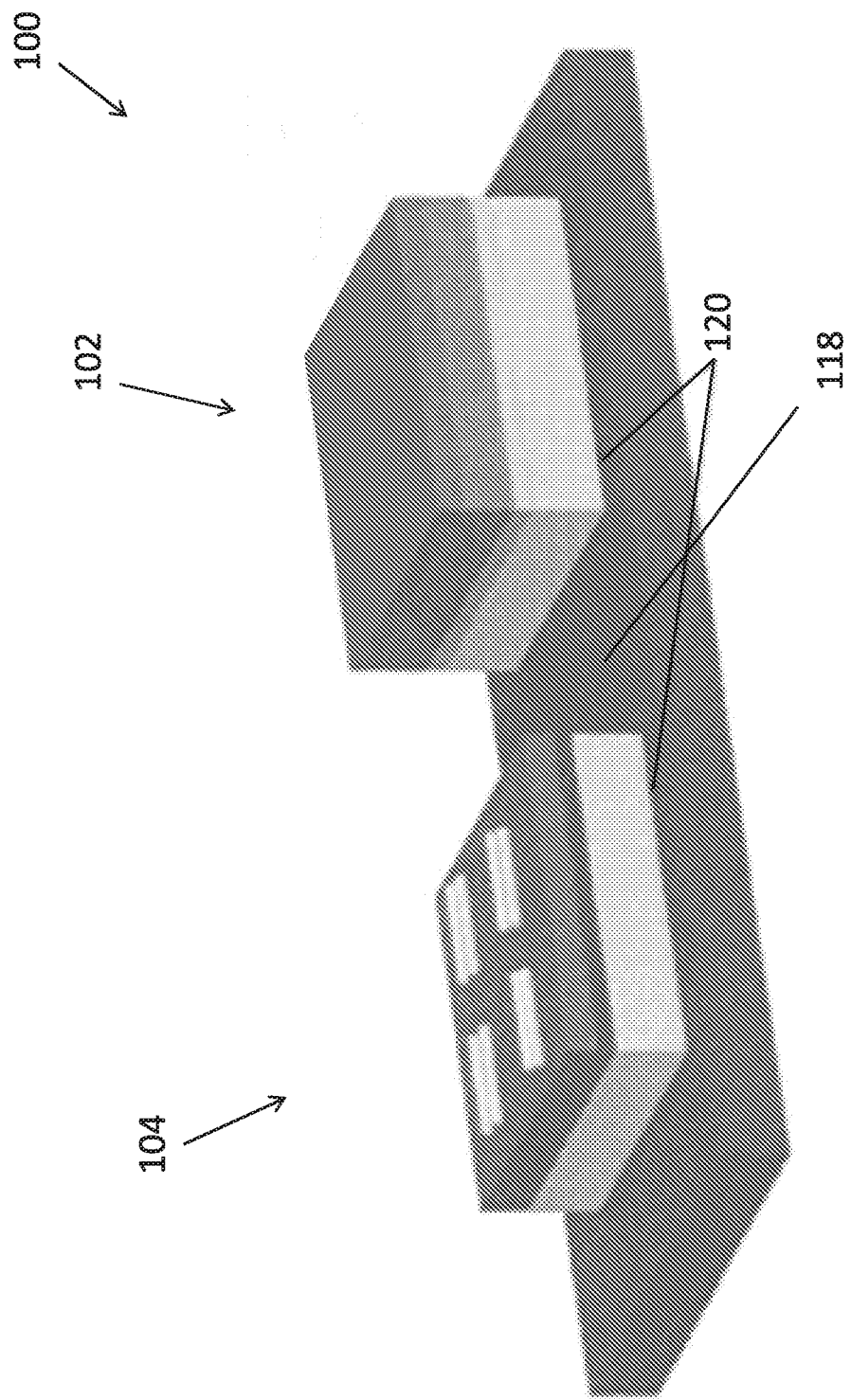
FIG. 1 is a perspective view of an electrochemical detector in accordance with one embodiment of the present invention.

With reference to FIG. 1, there is shown an example embodiment of an electrochemical detector 100 comprising at least one substance selection structure 102 disposed adjacent or proximate to an electronic device structure 104, wherein the substance selection structure 102 is arranged to interact with a target substance so as to alter an electrical characteristic of the electronic device structure 104.

In this embodiment, the electrochemical detector 100 comprises a substance selection structure 102 which includes chemical receptors arranged to interact with other chemical substance which is in contact with the substance selection structure 102, and the interaction is transformed to an electrical signal which may be further captured or detected by an electronic device structure 104. For example, a drop of analyte solution may be disposed on a surface of the substance selection structure 102, chemical receptors in the substance selection structure 102 may react with the target substance in the analyte solution, and the substance selection structure 102 may produce an electrical signal to be detected by the electronic device structure 104 upon the chemical reaction.

Preferably, the electrochemical detector 100 may comprise multiple substance selection structures 102 so as to improve the sensitivity and/or detection limit of the detection and/or to enable the detector to detect multiple target substances. Alternatively, the electrochemical detector 100 may include a single substance selection structure 102.

Each of the at least one substance selection structure 102 includes an ion-selective electrode, such that the substance selection structure 102 may interact with at least one electrically charged chemical ion of the target substance. For example, the ion-selective electrode 102 may be specifically designed for facilitating the detection of lead (II) ion in the target substance, and the ion-selective electrode 102 may include different structures and/or components for the detection of different target substances.

Figure 2:
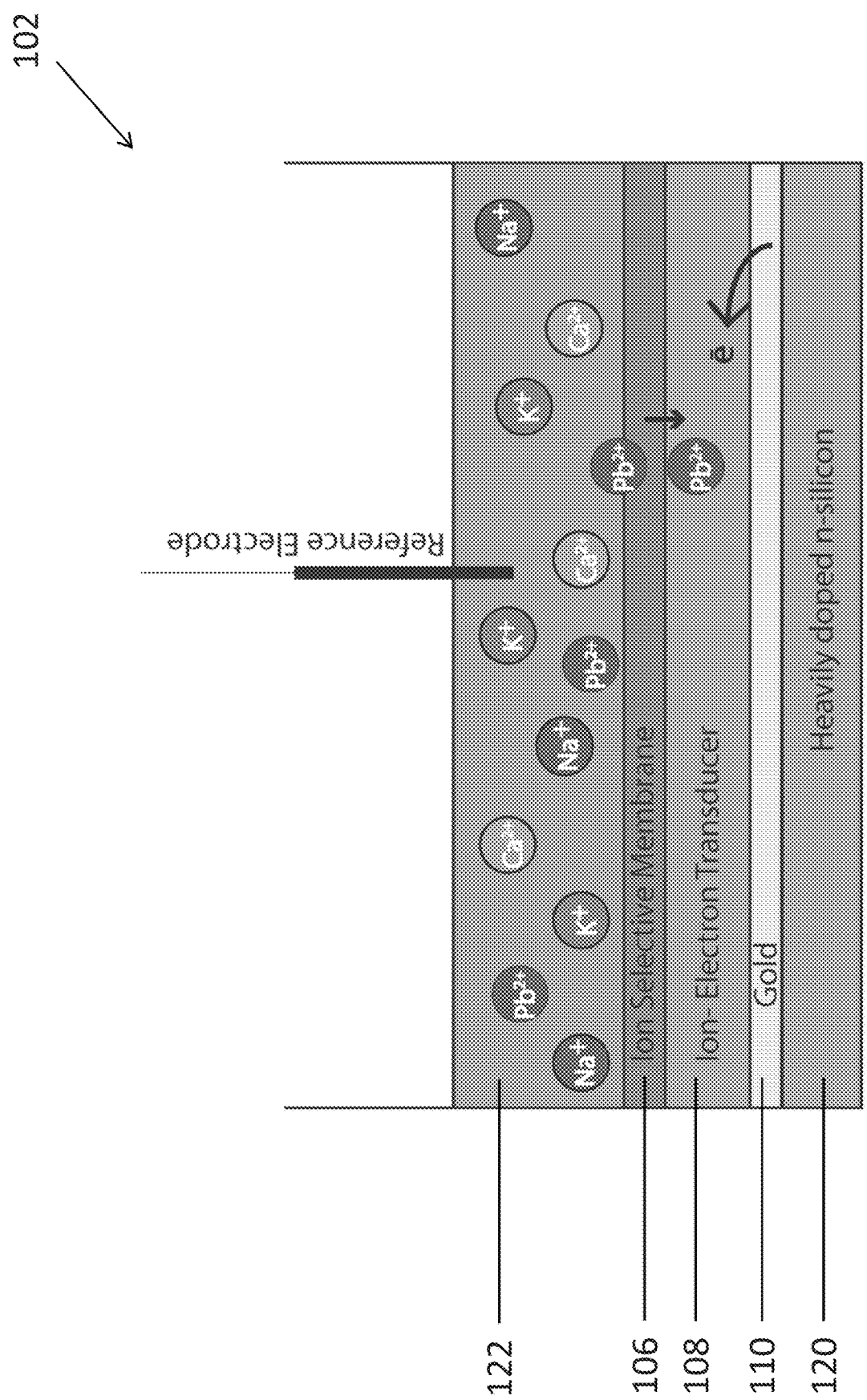
FIG. 2 is an illustration showing a cross-section of the substance selection structure and an interaction of between a target substance and the substance selection structure of the electrochemical detector of FIG. 1.

With reference to the example embodiment as shown FIG. 2, the ion-selective electrode 102 comprises an ion-selective membrane 106 and an ion-electron transducer 108. The ion-selective membrane 106 includes an ionophore and the ionophore may selectively chelate with at least one electrically charged chemical ion when a target substance is in contact with the ion-selective membrane 106. The ionophore may further transport the charged ion across the ion-selective membrane 106 (from the analyte solution to the ion-electron transducer 108 layer underneath as shown in FIG. 2 according to an effect of diffusion.

Upon the interaction between the target substance and the substance selection structure 102, the difference in analyte activity between the sample and the ion-selective membrane 106 generates a potentiometric signal that is related to a concentration of ions in the analyte solution or the target substance.

The ion-selective electrode 102 further comprises an ion-electron transducer 108 adjacent to the ion-selective membrane 106. When the transported ions reach the interface between the ion-electron transducer 108 and the ion-selective membrane 106, the charged ions dissociate from the ionophore, subsequently the ion-electron transducer 108 may receive the electrically charged ions at the interface. In response to the reception of the charged ions in the interaction between the target substance and the substance selection structure 102, the ion-electron transducer 108 transfers corresponding numbers of electrons and thus generates a potentiometric signal. The potentiometric signal is captured by a connected conductive layer 110 such as metal, and may be further processed or detected.

Preferably, the ion-selective membrane 106 may include a polymer film with a predetermined amount of selected ionophore. The ion-electron transducer 108 may include a PEDOT:PSS layer or any conducting polymer such as polypyrrole or poly 3-octylthiophene. Preferably, the conducting polymer improves signal stability owing to the redox capacitance of the ion-electron transducer 108 layer, and is de-doped upon reaction with analyte ions and released electrons.

In an example operation, the ionophore in the ion-selective membrane 106 selectively forms complexes with the target ion (Pb (II)) from the analyte solution. These charged complexes due to diffusion mobility are transported with the ion-selective membrane 106 towards the ion-electron transducer 108 layer. At the interface, the ion dissociates from the ionophore and enters the ion-to-electron transducer layer 108. From this transduction layer 108 an electron is transferred corresponding to the input of an ion from the ion-selective membrane 106. This transferred electron is captured by an electrically conductive layer 110 such as gold, silver, carbon or a high workfunction metal, and is the captured signal or electrons may be further transported to other parts of the sensor for processing.

Preferably, the captured electron and/or the potentiometric signal generated by the ion-electron transducer 108 of the substance selection structure 102 are further transmitted to the electronic device structure 104, such that the electrical characteristic of the electronic device structure 104 is altered.

In one example embodiment, the electronic device structure 104 is a thin-film transistor (TFT). An electronic transistor or a TFT may be characterized by different electrical characteristics such as threshold voltage (or turn on voltage) and source-drain current under different predetermined (gate and source-drain) voltage bias conditions.

When the substance selection structure 102 and the TFT 104 are electrically connected, the substance selection structure 102 may operate as a gate electrode of the TFT 104. In such configuration, the electrons transferred or the potentiometric signal generated by the ion-electron transducer 108 may contribute partly or entirely the gate voltage signal of the TFT 104. For example, the electrons may contribute to the gate voltage bias as an additional negative bias, and therefore the threshold voltage of the TFT 104 may then be changed, or the source-drain current across the source and drain electrodes may be increased/decreased when compare to the drain current under a same external gate/source/drain voltage bias applied to the transistor without the extra electrons.

Preferably, the electronic device structure 104 may comprises an active layer 112 such as a TFT material including silicon, a compound semiconductor, metal oxide semiconductor (e.g. zinc oxide) or an organic material such as copper hexadecafluorophthalocyanine (F16CuPc). A layer of dielectric material 114 may be included to serve as the gate dielectric of the TFT, and may include oxides such as $SiO_2$, $HfO_2$ and/or $Al_2O_3$. The source/drain electrodes 116 may include typical conductive metals with suitable work functions such as Au, Ag and or Al.

The electronic device structure 104 and the substance selection structure(s) 102 are electrically and/or physically connected, such that electrical signal may be transmitted between different individual structures. Preferably, the electrochemical detector 100 further comprises an intermediate substrate 118 arranged to connect one or more substance selection structure 102s and/or the electronic device. For example, the intermediate substrate 118 may include a copper substrate, or it may include an electrically conductive substrate, such as but not limited to a metal substrate and a heavily doped semiconductor substrate. The intermediate substrate 118 may also provide mechanical support to different structures disposed thereon.

Figures 3A, 3B:
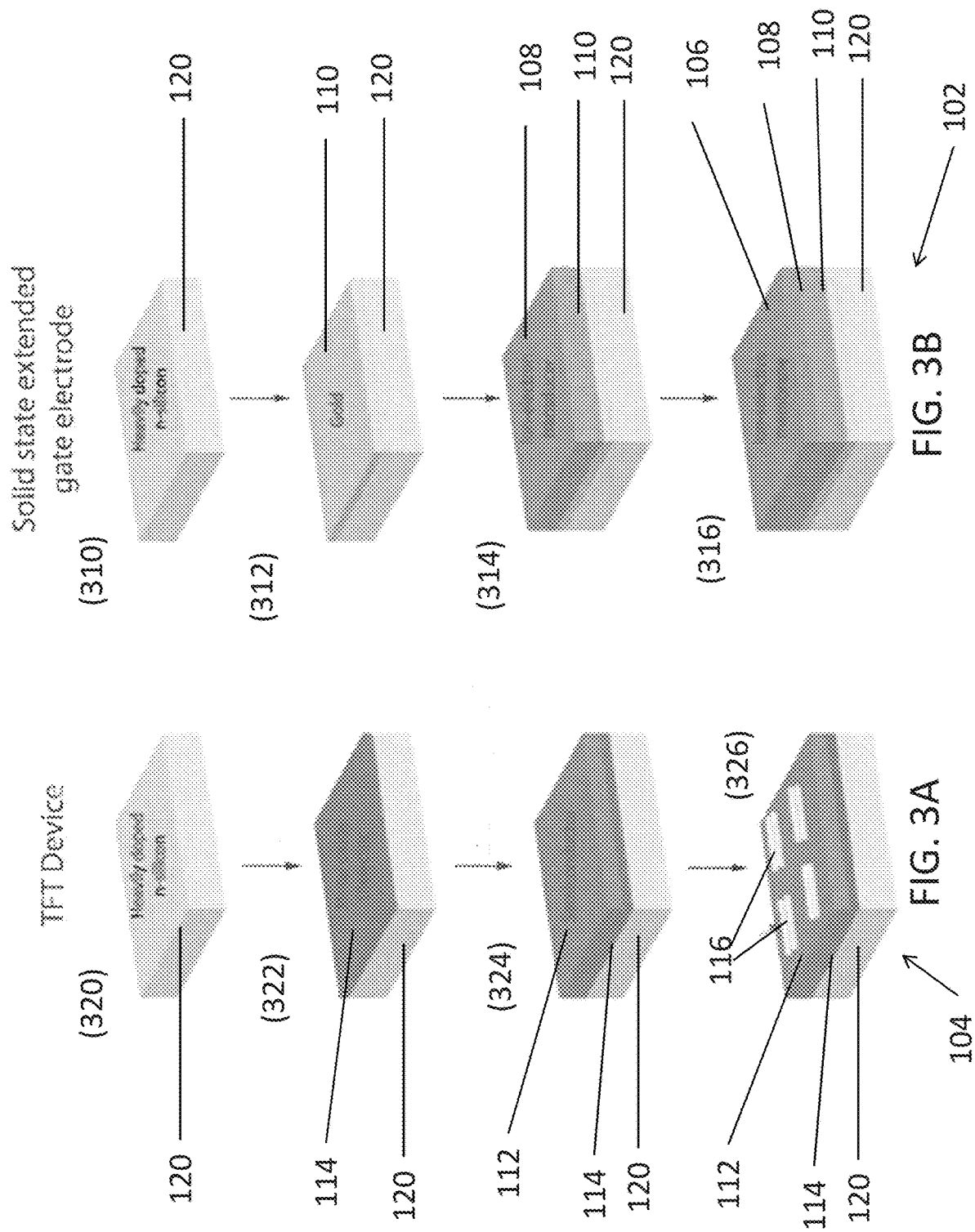
FIG. 3A is an illustration showing a process flow of fabrication of an electronic device structure of the electrochemical detector of FIG. 1.
FIG. 3B is an illustration showing a process flow of fabrication of a substance selection structure of the electrochemical detector of FIG. 1.
Figure 3C:
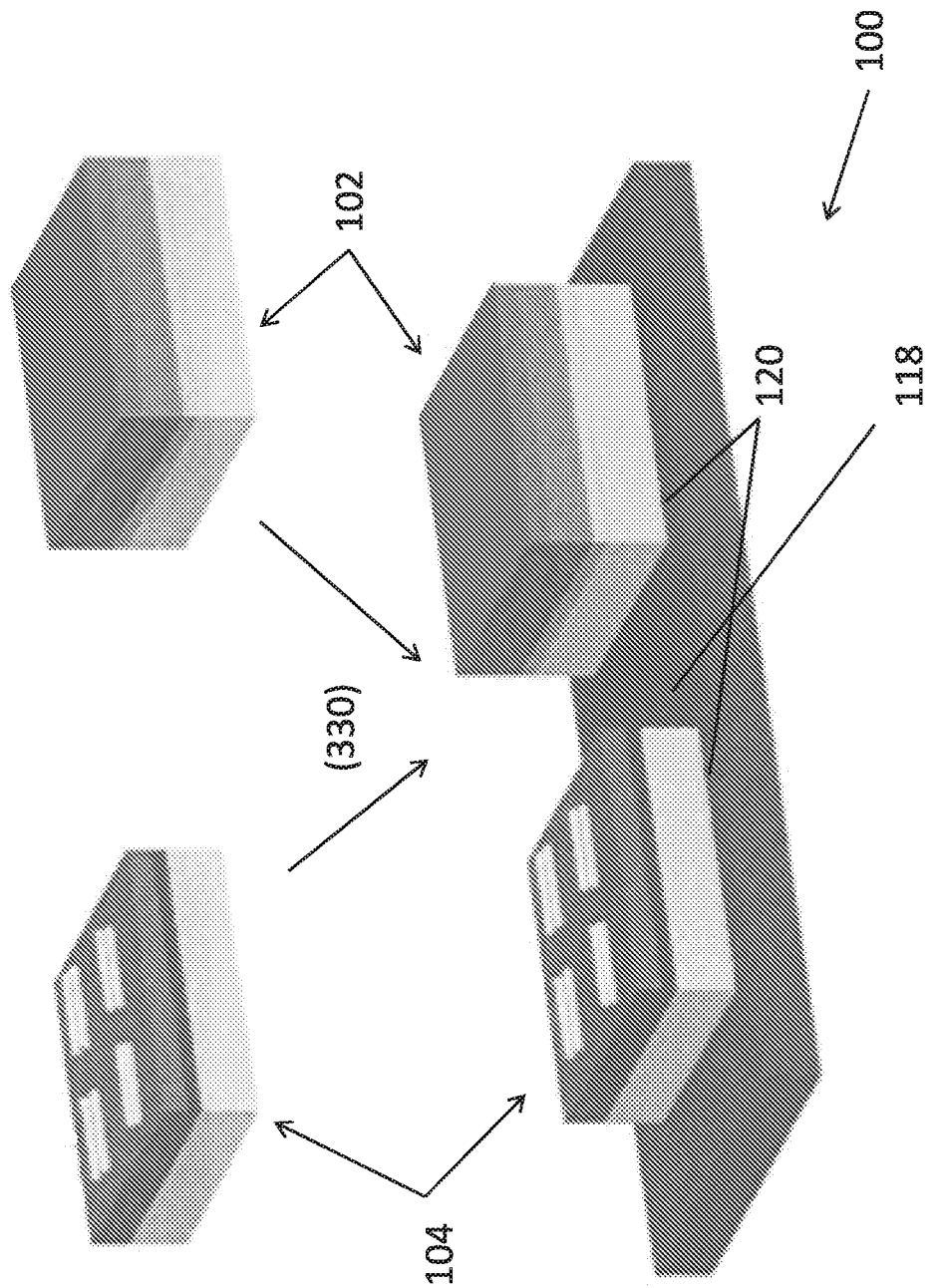
FIG. 3C is an illustration showing the combination of the electronic device structure of FIG. 2A and the substance selection structure of FIG. 2B in the fabrication of the electrochemical detector of FIG. 1.

With reference to FIGS. 3A to 3C, there is shown an example embodiment of a fabrication of the electrochemical detector 100. In this embodiment a substance selection structure 102 and an electronic device structure 104 are fabricated on a plurality of separate substrates 120 (such as heavily doped semiconductor substrates or metal substrates), and the two fabricated structures are physically and electrically connected to an intermediate copper substrate 118.

To fabricate the substance selection structure 102, at step 310, a heavily n-doped (n+) silicon substrate 120 is cleaned with standard cleaning procedures. At step 312 a layer of Au 110 (30 nm-50 nm) is deposited on the silicon substrate 120 using thermal evaporation. Various known methods may be applied to deposit Au or other metal layer, such as but not limited to e-beam evaporation, sputtering, chemical vapor deposition, etc. For layers which may be deposited using solution process (such as metal or carbon ink), methods such as sol-gel, spin coating, ink-jet printing, screen printing, spray coating, drop casting, etc. may be applied.

At step 314, a layer of conductive polymer such as PEDOT:PSS may be deposited on the Au layer 110 using electropolymerization or drop casting (or any alternative solution process listed above). Preferably, the dried conductive polymer layer forms the ion-electron transducer 108 layer with a thickness of 0.5 µm-1 µm.

At step 316, an ion-selective membrane cocktail (mixture) is prepared and drop-cast on the ion-electron transducer layer 108. The mixture is then dried to form the ion-selective membrane 106 with a thickness of 1 µm-5 µm. An example ion-selective membrane cocktail may be prepared by mixing of 1% wt. lead ionophore IV, 0.75 wt % potassium tetrakis (4-chlomphenyl) borate (KTChP), 32.25 wt % polyvinyl chloride (PVC) and 66 wt % 2-nitrophenyl octyl ether (oNPOE) plasticizer in 2 mL of tetrahydrofuran (THF). Alternatively, other suitable deposition methods may be applied.

To fabricate the TFT structure 104, at step 320, an n+ silicon substrate 120 is cleaned with standard cleaning procedures. At step 322, the metal-oxide dielectric (e.g. $HfO_2$, $Al_2O_3$) layer 114 is coated on top of the silicon substrate 120 using either solution process sol-gel method (spin coating, printing. etc.) or atomic layer deposition (ALD), and preferably the dielectric layer 114 has a thickness of 5 nm-10 nm. Preferably, such dielectric layer may operate as a gate dielectric of the TFT device.

At step 324, a semiconductor layer 112 (n-type semiconductor) is deposited using thermal evaporation or formed through a solution process sol-gel method (spin coating, printing. etc.) or any other suitable fabrication methods as discussed earlier. In this process, 30 nm-50 nm of semiconductor layer 112 is formed on top of the gate dielectric layer 114, which may operate as the active layer of the TFT device.

At step 326, gold or other suitable metal pads 116 are deposited on the semiconductor layer which form the source and drain electrodes of the TFT device 104. The metal pads 116 may be deposited with thermal evaporation through a shadow-mask with the desired patterns. Alternatively, a conformal layer of metal may be patterned using conventional photolithography approaches and other suitable deposition methods to form the metal pads 116. Preferably, the metal pads 116 may include a thickness of 30 nm-50 nm.

The abovementioned ranges of thickness of different layers may be changed in according to requirements or applications of the electrochemical detector 100. For example, increasing the thickness of the ion-selective membrane 106 or the ion-electron transducer 108 may increase the sensitivity of the electrochemical detector 100, with a side-effect that the response time may become longer.

The fabricated substance selection structure 102 and TFT structure 104 may be connected to the intermediate copper substrate 118 at step 330. For example, conductive adhesive may be applied to connect the two structures, either on the same side or opposite sides, to the copper substrate 118. In such configuration, the substance selection structure 102 may operate as an extended gate electrode of the TFT device 104. Alternatively, the substance selection structure 102 and the TFT structure 104 may be connected without an intermediate substrate 118, or the two different structures may be fabricated on the same substrate such as on a same side of a silicon substrate or on opposite sides on a double-side polished silicon substrate, in which the electrical signal between the two structures may be transmitted through the silicon substrate.

Figure 4B:
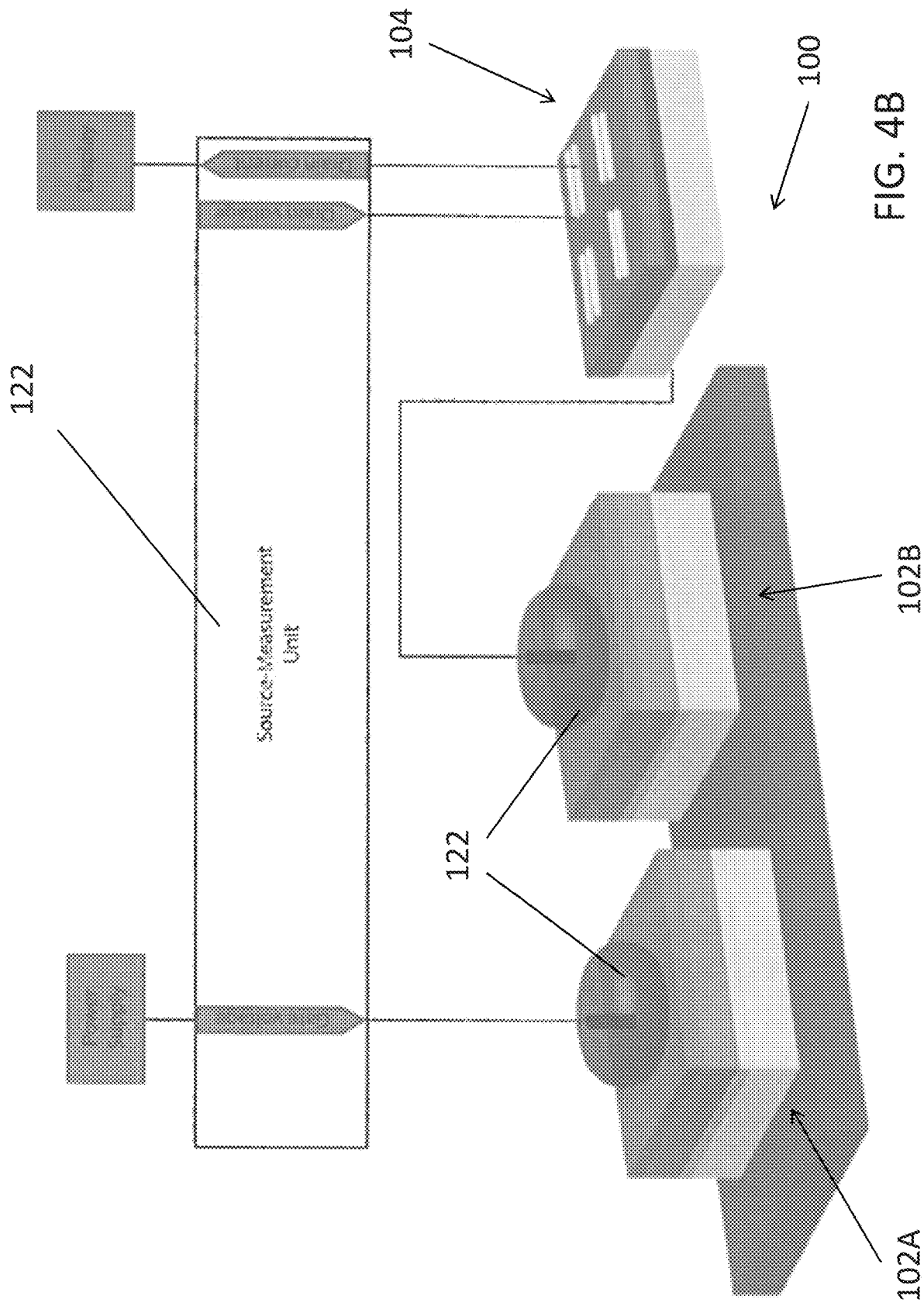
FIG. 4B is an illustration showing a second example operation of detecting a target substance with the electrochemical detector of FIG. 1.

With reference to FIGS. 4A and 4B, there is shown an embodiment of a method of detecting a target substance with an electrochemical detector 100. The method comprises the steps of: applying an analyte solution 122 containing a predetermined amount of the target substance to the at least one substance selection structure 102; applying a gate voltage to the thin-film transistor 104 via the analyte solution 122 and the at least one substance selection structure 102; applying a source-drain bias to the thin-film transistor 104; and determining a concentration of the target substance in the analyte solution 122 based on a characterization of the electrical characteristic of the thin-film transistor 104.

In this example, an analyte solution 122 which contains the target substance such as lead ion is applied on a surface of ion-selective membrane 106 of the substance selection structure 102. As discussed earlier in this disclosure, the interaction between the ionophore and the charged ions leads to a production of potentiometric signal which is transmitted to the adjacent or proximate TFT device 104 at the gate terminal and therefore the electrical characteristics such as threshold voltage and/or source-drain current are altered. Such change in electrical characteristics of the TFT device 104 corresponds to the concentration of the detected target substance in the analyte solution 122, and the change may be characterized by conventional electrical measurement unit for characterizing a transistor or other types of electronic devices.

For example, a high impedance (gigaohm) voltmeter, a nano-ammeter, a semiconductor parameter analyzer or an electrical source-meter unit (SMU) such as Keithley 2400 series may be used in the measurement steps. Example applied voltage bias may include a gate voltage of 3V and source-drain voltage of 3V. A small amount (such as 20-30 μL) of analyte solution is sufficient for the detection of the target substance.

Preferably, the sensing pad (the ion-selective membrane 106) may be conditioned prior to measurement. Firstly, the sensing pad is conditioned in 200 μL of 1:1 aqueous solution of 1000 ppm Pb (II) (2% $HNO_3$) for at least 12 hours. Secondly, the sensing pad is conditioned in 200 μL of 1:1 aqueous solution of 10 ppb Pb (II) (2% $HNO_3$) $HNO_3$ for at least 24 hours.

Figure 5A:
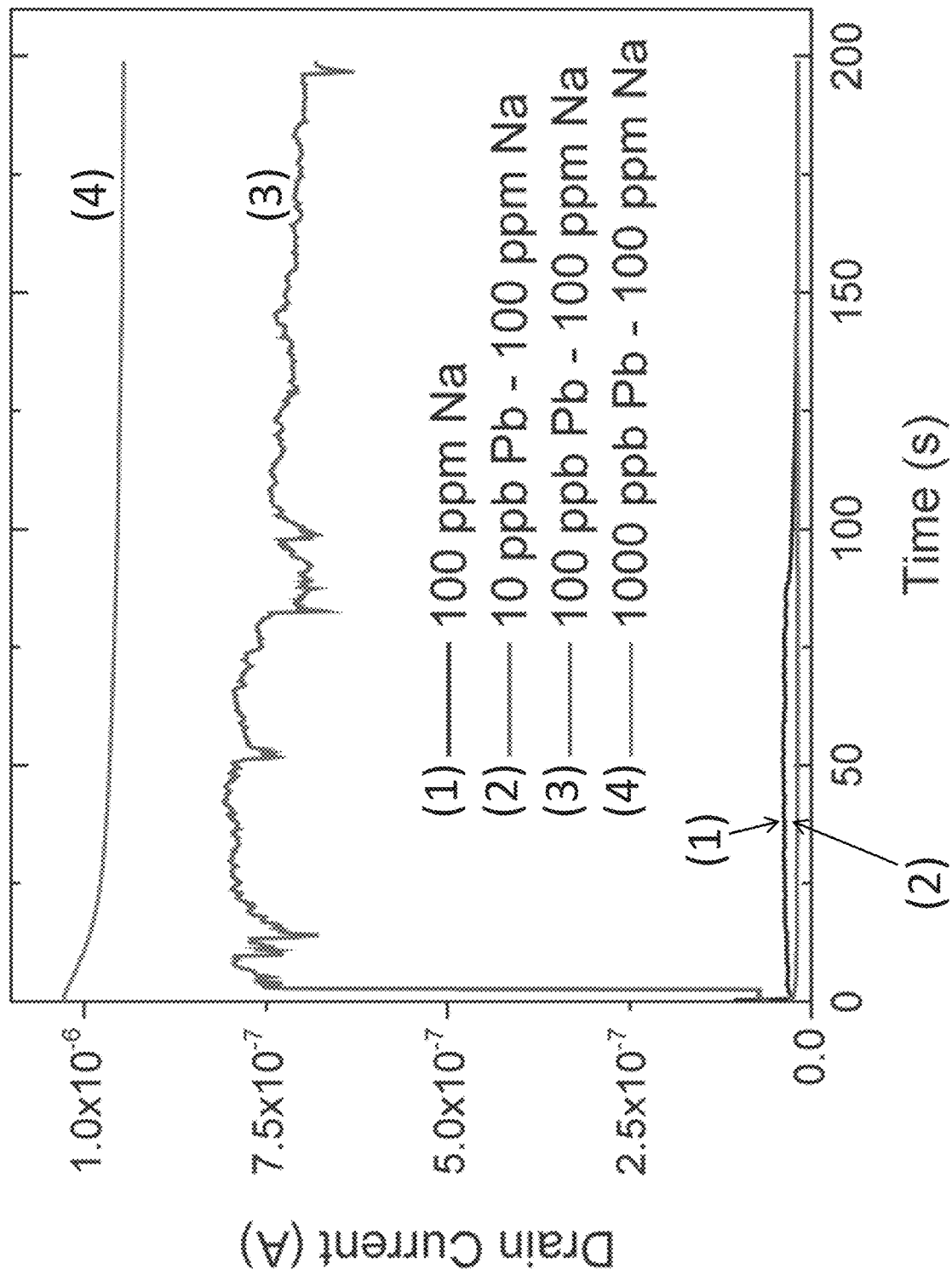
FIG. 5A is a plot showing a transient drain current curve for various concentrations of target substances based on the first example operation of detecting a target substance of FIG. 4A.

In a first example measurement setup, referring to FIG. 4A, the analyte solution 122 is dropped on the extended gate sensor. A reference electrode is dipped into the sample solution 122. Using an SMU unit 124, a positive gate voltage is applied though the reference electrode and at the same time a positive drain-source voltage is applied to the TFT device 104. The signal is read out as a function of the threshold voltage shift of the TFT device 104 or the change in saturation drain current at a fixed gate voltage and source-drain voltage. With reference to FIG. 5A, there is shown a measurement result of the setup for the detection of 0, 10, 100 and 1000 ppb Pb (II) ions with 100 ppm Na ions in an analyte solution 122 with drain current range in the order of $10^{-7}$ to $10^{-6}$ A.

To enhance the sensitivity and/or the detection limit of the target substance in the electrochemical detector 100, two or more substance selection structures 102 may be included to co-operate with the electronic device structure 104. Preferably, at least two of the substance selection structures 102 may be electrically connected in a serial configuration in a gate electrode of the thin-film transistor 104. In such configuration an overall capacitance subjected by the thin-film transistor 104 is reduced and thus the detection limit of the determination of the concentration of the target substance is decreased.

Unlike the measurement setup from the first example measurement setup as shown in FIG. 4A, the gate voltage is applied to the analyte solution 122 applied on a first substance selection structure 102 and the thin-film transistor 104 is electrically connected to a second substance selection structure 102 via the analyte solution 122 applied on the second substance selection structure 102. The first and the second substance selection structures are electrically connected by an intermediate copper substrate 118 at the back side of the silicon substrates 120.

In a second example measurement setup, referring to FIG. 4B, two extended gate sensors are connected in series. First the analyte solution 122 is dropped on both extended gate sensing pads 102. A reference electrode connected to a voltage source is dipped into the solution 122 on the first sensing pad 102A. A second reference electrode in electrical connection to the bottom gate of the TFT device 104 is dipped into the solution 122 on top of the second sensing pad 102B. A SMU unit 124 supplies the gate voltage through the reference electrode on the first sensing pad 102A and drains voltage through source and drain contacts on TFT device 104. The signal is read out as a function of the threshold voltage shift of the TFT device 104 or the change in saturation drain current at a fixed gate voltage and source-drain voltage.

Figure 5B:
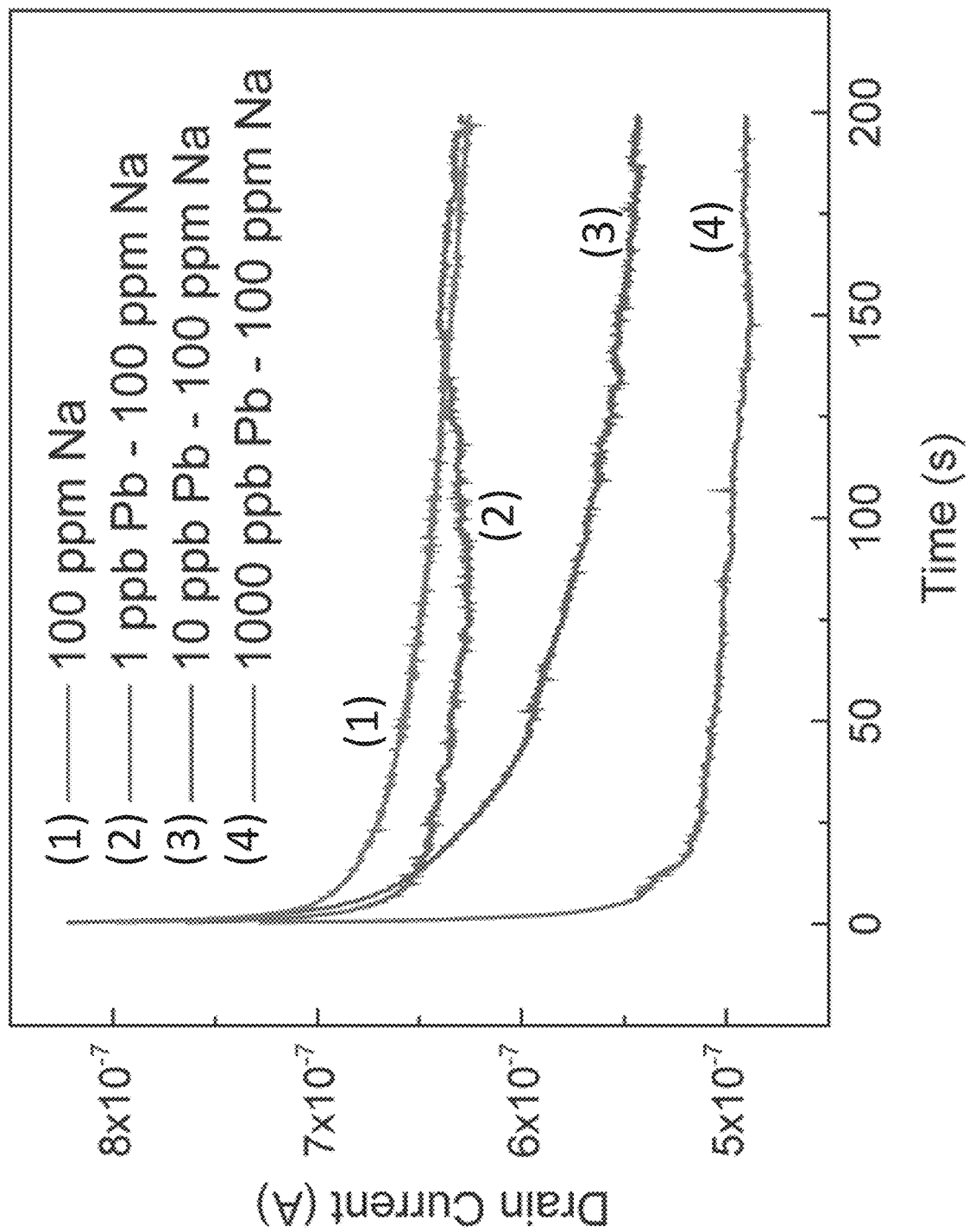
FIG. 5B is a plot showing a transient drain current curve for various concentrations of target substances based on the second example operation of detecting a target substance of FIG. 4B.

With reference to FIG. 5B, down to 10 ppb (parts-per-billion) levels of Pb (II) ions has been detected (with 100 ppm Na ion as interfering ion). The connection of two extended gates in series lowers the overall effective capacitance of the circuit and thus decrease the detection limit of the electrochemical detector 100.

Alternatively, more sensing pads or substance selection structures 102 may be connected in parallel (or increasing the sensing area of the sensing pads) so as to improve the sensitivity of the device. This may allow more target substance to contact with the ion-selective membrane 106 thus a potentiometric signal with higher amplitude is generated. However, the detection limit remains the same in such modification.

These embodiments are advantageous in that the electrochemical detector may be used in various applications including detection of harmful or toxic substances such as Pb (II) ions in water. It may be implemented in portable electronic devices and hand-held sensors which may be used in domestic applications. The low-voltage operation of the electrochemical detectors ensures chemical stability (no induced electrolysis) of analyte solutions.

Advantageously, the performance of the detection shows that the electrochemical detector has high selectivity and sensitivity for target ions with the ion-selective solid state electrode. The solid-state ion selective electrode may be easily tuned for selectively sensing different ions (reversible & non-reversible), such as but not limited to sodium, mercury and potassium by including different ionophore (receptors) in the ion-selection membrane. In addition, solid-state ion-selective electrode (the extended gate) requires no internal filling solution.

The fabrication process is also simple and the electrochemical detector may be readily fabricated using different simple fabrication processes including low-cost fabrication methods such as printing and solution processing with low-cost materials. In addition, the substance selection structure and the electronic device structure may be separately fabricated on different substrates which may further simply the fabrication process involved. The fabrication of the electrochemical detectors may be easily scaled up.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Any reference to prior art contained herein is not to be taken as an admission that the information is common general knowledge, unless otherwise indicated.

The invention claimed is:

1. An electrochemical detector comprising at least one substance selection structure disposed adjacent or proximate to an electronic device structure, wherein the at least one substance selection structure and the electronic device structure are fabricated on a plurality of separate substrates; and an intermediate substrate connecting the at least one substance selection structure and the electronic device structure; wherein the substance selection structure is arranged to interact with a target substance so as to alter an electrical characteristic of the electronic device structure,
wherein the at least one substance selection structure is arranged to interact with at least one electrically charged chemical ion of the target substance;
wherein each of the at least one substance selection structure includes an ion-selective electrode;
wherein the ion-selective electrode comprises an ion-selective membrane arranged to selectively chelate with the at least one electrically charged chemical ion, and wherein the target substance is in contact with the ion-selective membrane;
wherein the ion selective electrode further comprises an ion-electron transducer arranged to generate a potentiometric signal in response to the interaction between the target substance and the substance selection structure; and
wherein the ion-electron transducer includes a conductive polymer.

2. An electrochemical detector in accordance with claim 1, wherein the ion-selective membrane includes an ionophore.

3. An electrochemical detector in accordance with claim 1, wherein the ionophore is arranged to selectively chelate with the at least one electrically charged chemical ion so as to transport the at least one electrically charged ion across the ion-selective membrane according to an effect of diffusion.

4. An electrochemical detector in accordance with claim 1, wherein the ion-electron transducer is adjacent to the ion-selective membrane.

5. An electrochemical detector in accordance with claim 1, wherein the ion-electron transducer is arranged to receive the at least one electrically charged ion dissociated from the ionophore at an interface between the ion-electron transducer and the ion-selective membrane.

6. An electrochemical detector in accordance with claim 1, wherein the ion-electron transducer is arranged to generate the potentiometric signal by transferring at least one electron in response to the reception of the at least one electrically charged ion.

7. An electrochemical detector in accordance with claim 1, wherein the potentiometric signal generated by the ion-electron transducer is further transmitted to the electronic device structure so as to alter the electrical characteristic of the electronic device structure.

8. An electrochemical detector in accordance with claim 1, wherein the electronic device structure is a thin-film transistor.

9. An electrochemical detector in accordance with claim 8, wherein the at least one substance selection structure is arranged to operate as a gate electrode of the thin-film transistor.

10. An electrochemical detector in accordance with claim 8, wherein the electrical characteristic includes a threshold voltage of the thin-film transistor.

11. An electrochemical detector in accordance with claim 8, wherein the electrical characteristic includes a saturation drain current across the thin-film transistor under a predetermined gate bias and a predetermined source-drain bias.

12. A method of detecting a target substance with the electrochemical detector in accordance with claim 8, comprising the steps of:
electrically connecting at least two substance selection structures in a serial configuration in a gate electrode of the thin-film transistor;
applying an analyte solution containing a predetermined amount of the target substance to the at least one substance selection structure;
applying a gate voltage to the thin-film transistor via the analyte solution and the at least one substance selection structure;
applying a source-drain bias to the thin-film transistor; and
determining a concentration of the target substance in the analyte solution based on a characterization of the electrical characteristic of the thin-film transistor.

13. A method of detecting a target substance in accordance with claim 12, wherein the gate voltage is applied to the analyte solution applied on a first substance selection structure and the thin-film transistor is electrically connected to a second substance selection structure via the analyte solution applied on the second substance selection structure.

14. A method of detecting a target substance in accordance with claim 12, wherein an overall capacitance subjected by the thin-film transistor is reduced such that the detection limit of the determination of the concentration of the target substance is decreased.

15. An electrochemical detector in accordance with claim 1, wherein the target substance includes lead ion.

16. An electrochemical detector in accordance with claim 1, wherein the intermediate substrate includes a copper substrate.

17. An electrochemical detector in accordance with claim 1, wherein the intermediate substrate is further arranged to transmit an electronic signal between the at least one substance selection structure and/or the electronic device structure.

18. An electrochemical detector comprising:
  at least one substance selection structure disposed adjacent or proximate to an electronic device structure, wherein the at least one substance selection structure and the electronic device structure are fabricated on a plurality of separate substrates; and
  an intermediate substrate connecting the at least one substance selection structure and the electronic device structure;
  wherein the substance selection structure is arranged to interact with a target substance so as to alter an electrical characteristic of the electronic device structure, wherein the plurality of separate substrates includes a plurality of doped silicon substrates.

19. An electrochemical detector in accordance with claim 18, wherein the intermediate substrate includes a copper substrate.

20. An electrochemical detector in accordance with claim 18, wherein the intermediate substrate is further arranged to transmit an electronic signal between the at least one substance selection structure and/or the electronic device structure.

21. An electrochemical detector in accordance with claim 18, wherein the electronic device structure is a thin-film transistor.

22. An electrochemical detector in accordance with claim 18, wherein the target substance includes lead ion.

* * * * *